(12) United States Patent
Doerr et al.

(10) Patent No.: US 8,423,135 B2
(45) Date of Patent: Apr. 16, 2013

(54) MRT-ADJUSTED IEGM-SCANNING (75) Inventors: Thomas Doerr, Berlin (DE); Ingo Weiss, Berlin (DE)

(73) Assignee: Biotronik CRM Patent AG, Baar (CH)

(*) Notice: Subject to any disclaimer, the term of this patent is extended or adjusted under 35 U.S.C. 154(b) by 146 days.

(21) Appl. No.: 12/972,449

(22) Filed: Dec. 18, 2010

(65) Prior Publication Data
US 2011/0153011 A1 Jun. 23, 2011

Related U.S. Application Data (60) Provisional application No. 61/288,858, filed on Dec. 22, 2009.

(51) Int. Cl.
*A61N 1/36* (2006.01)
*A61N 1/16* (2006.01)

(52) U.S. Cl.
USPC ............................................................ 607/4

(58) Field of Classification Search ................. 607/1–4
See application file for complete search history.

(56) References Cited

U.S. PATENT DOCUMENTS

| 2003/0144705 | A1* | 7/2003 | Funke ............................. 607/27 |
| 2004/0193224 | A1 | 9/2004 | Hedberg et al. |
| 2004/0263172 | A1 | 12/2004 | Gray et al. |
| 2005/0070787 | A1 | 3/2005 | Zeijlemaker |
| 2006/0047216 | A1 | 3/2006 | Dorr et al. |
| 2006/0293591 | A1 | 12/2006 | Wahlstrand et al. |
| 2008/0154342 | A1 | 6/2008 | Digby et al. |

OTHER PUBLICATIONS

European Search Report dated Apr. 27, 2011 (8 pages).

* cited by examiner

*Primary Examiner* — Carl H Layno
*Assistant Examiner* — Paula J Stice
(74) *Attorney, Agent, or Firm* — ARC IP Law, PC; Joseph J. Mayo (57) ABSTRACT A device and a method for working with electromagnetic fields, specifically those fields that occur in image-guided nuclear spin tomography examinations (MRT or MRI). More precisely, the invention concerns an at least partially implanted medical device (IMD) that permits the delivery of electrical stimulation impulses by an electrode only in timeframes, in which no electromagnetic interferences are recognized and/or the control unit performs a reconstruction of electrical measurements for the timeframes in which electromagnetic interferences are recognized.

15 Claims, 8 Drawing Sheets

FIG. 1

PRIOR ART

MRT-ADJUSTED IEGM-SCANNING

This application claims the benefit of U.S. Provisional Patent Application 61/288,858, filed on Dec. 22, 2009, which is hereby incorporated by reference in its entirety.

BACKGROUND OF THE INVENTION

1. Field of the Invention

Embodiments of the invention relate to a device and a method for working with electromagnetic fields, specifically those fields that occur in image-guided nuclear spin tomography devices. ("MRT" or "MRI" stand for magnetic resonance tomography and magnetic resonance imaging respectively, wherein these two acronyms are used interchangeably herein).

2. Description of the Related Art

Although MRI examinations are becoming increasingly important in diagnostic medicine, some patients are contraindicated for MRI exams. Such a contraindication can be the result of an at least partially implanted medical device (hereinafter also implant or IMD). In addition to the MRI examinations, other technical applications also present a danger for the users of medical devices or implantable medical devices, particularly when these generate strong electromagnetic interference fields (EMI, Electro Magnetic Interference) in the surrounding area.

To make MRI examinations possible in spite of that, various approaches are known that relate either to conducting the MRI examination or to the implantable medical device.

Among others, technologies for the recognition of magnetic fields are known that are based on conventional methods for detecting magnetic fields. Thus, US 2008/0154342 describes a process using a GMR sensor (Giant Magnetic Resistance) for recognizing problematic magnetic fields of MRT devices. This technological methods are, however, not very specific and generate an increased requirement of energy, which leads to a shorter service life for the same energy reserves.

Also known in prior art is publication US 2005/0070787, which describes a setup that coordinates switching off certain components of an implanted medical device that are switched off during the delivery of electromagnetic irradiation impulses. To do so, a communication from the MRI device to the implant is required in which the information of the chronological progression from the MRI device to the implant are transmitted. Up to now, such a communication between implant and MRI devices is not provided so that an application is possible only after an upgrading of MRI devices and implants or at least of the MRI devices. Further, prior art does not make any additional solutions available that replace the components that are switched off, by means of which an adapted operating mode of an implanted medical device and/or a continual monitoring process of the physiological parameters of an implant carrier is not ensured in each case. Additionally, prior art is dependent because of the necessary communication between implant and MRI device, as a consequence of which other sources of interference are not recognized and cannot be taken into consideration during operation.

BRIEF SUMMARY OF THE INVENTION

It is therefore the object of embodiments of the invention to eliminate the deficiencies of prior art and to provide a device that makes high reliability possible in the presence of electromagnetic interferences (EMI, Electro Magnetic Interference). The object is solved by an at least partially implantable medical device (IMD) as claimed herein.

At the same time, the at least partially implanted medical device (IMD) includes at least one unit for recognizing electromagnetic interferences, containing at least one sensor or indicator for electromagnetic interference fields and at least one timer, at least one control unit that can be connected with the unit for recognizing electromagnetic interferences, at least one electrode line that is connected with the control unit, and that is provided with an electrode at the other end that is in contact with the body tissue, and whereby the electrode either extends into the interior of the body or is located on the surface of an implant, whereby the control unit permits the delivery of electrical stimulation impulses by the at least one electrode only in timeframes, in which no electromagnetic interferences are recognized and/or the control unit performs a reconstruction of the electrical measurements captured by the at least one electrode for the timeframes in which the electromagnetic interferences are recognized.

Thereby, completely implanted systems, as well as those in which only components, for example, but not limited to, electrodes, including parts of the electrode lines and/or optical conductors, with sensors and/or actuators and/or stimulators, and/or lines of internal or external medication pumps and/or fluid pumps for diagnosis and/or therapy are covered by the term: at least partially implanted.

On the one hand, the fluid pumps can be suitable for pumping fluids out of the interior of the body to an analysis unit and/or therapy unit that can be located inside, as well as outside of the body.

It is preferred, that the at least partially implantable medical device is an external cardiac pacemaker and/or an external defibrillator or implanted cardiac pacemaker and/or defibrillator/cardioverter and/or a cardiac resynchronization therapy device (CRT), a cardiac support system such as a heart support pump, an artificial heart, a neurostimulator, an implantable monitoring device (patient monitor), an implantable medication pump, an implanted fluid pump and/or an external heart-lung system, and that the control unit of the IMD selects the operating condition of the IMD using the detected electromagnetic interference values and/or the measured values detected by the at least one electrode and/or the reconstructed measured values from predetermined operating conditions.

It is also preferred that the timer has a storage device that is configured for storing time differences such as therapy intervals and/or intervals of intrinsic system events. Thereby, therapy intervals are to be understood as intervals in which therapies are delivered, whereby individual therapies as well as groups of therapies are included. Therapy intervals are, for example, but not limited to, RR time or QT time or TQ time or a corresponding parameter tuple from an IEGM. Even for intervals of intrinsic system events, various intervals are possible such as, but not limited to individual system events and/or groups of system events such as QRS complexes or other complexes or complete cardiac cycles and/or pathological events. In general, a person skilled in the art understands IEGM to mean intracardiac electrocardiogram.

It is especially preferred that the chronological distance between two electrical stimuli is a therapy interval and that at least the respectively preceding therapy interval can be stored.

It is also especially preferred that the storage device is organized as "first in first out" (FIFO).

It is also preferred that the control unit calculates the point in time of the next therapy with the data of the timer.

It is especially preferred that the calculation of the point in time for the next therapy is based on a cardiac rhythm estimate and/or a heart simulator.

Parameters for the models of the calculation of the points in time for therapy are programmable and/or the models for the calculation of the point in time for therapy include the IEGM measurements and/or EKG measurements and/or reconstructed IEGM measurements for calculation, whereby EKG data are determined using external tools and are made available to the at least partially implanted medical device and also data from the patient history from the information sources that are available such as, but not limited to, patient files, patient databases and/or patient devices, and/or the calculation is based on the parameters and measurements stored in the implant, specifically a long-term storage device and/or the calculation is based on the parameters and measurements stored in the implant during the capturing of which no electromagnetic interferences were detected.

It is also especially preferred that the calculation is based on an approximation model of cardiac restitution and/or a linear or nonlinear time series models and/or on a weighted average of n previous time differences where n is larger than or equal to 1.

The person skilled in the art understands cardiac restitution as meaning the connection between the action potential duration of heart muscle cells depending on the duration of the preceding diastolic interval—graphically illustrated it is also known as restitution curve. Conversely, when the diastolic interval is known, by using the restitution curve, the repolarization time of the following cardiac cycle can be estimated and thus the stimulation in the vulnerable phase can be avoided.

The reconstitution curve can be indicated in changed from, dependent on the preceding RR interval as well. In the simplest case, the curve represents only the static connection between the heart rate and the repolarization behavior. A model approach with greater depth of detail also considers the dynamic interconnections, i.e. the repolarization time also depends on the additional past of the cardiac activity (for example, but not limited to, several preceding heart rate intervals, as well as several preceding repolarization times), such as especially considered in this invention. This is called depth of memory. Thus, at its simplest, the law of restitution states:

$$RmTm = f(Rm-1Rm)$$

Or more general $RmTm=f([Rm-i-1Rm-i], [Rm-i-1Tm-i-i], [p]); i=0 \ldots N$, N=depth of memory, p=parameter vector that parameterizes this law.

It is further preferred that in the calculation of the next point in time for therapy, the vulnerable phases of the heart stimulation cycle are avoided and/or the parameters for the calculation models for the point in time for therapy are programmable and/or the calculation models for calculating points in time for therapy include the IEGM measurements and/or EKG measurements and/or the reconstructed IEGM measurements in the calculation, whereby EKG data are determined by external tools and are made available to the at least partially implanted medical device and also data from the patient history from available information sources are included, such as patient files, patient databases, and/or patient device, and/or the calculation is based on parameters and measurements that are stored in the implant, specifically in a long-term storage device and/or the calculation is based on parameters and measurements that are stored in the implant during the capture of which no electromagnetic interferences were detected. This embodiment is particularly relevant in the context of so-called home monitoring in which data from an implant are sent to a central location at predetermined intervals and are made available from there or are also made available to the physician directly. With this embodiment it can be ensured that only valid data are forwarded to the patient databank or the physician.

It is also preferred that the stimulation unit can be triggered and/or retriggered, specifically by measurements in timeframes without detected electromagnetic interference fields and/or by reconstructed measured data between timeframes without detected electromagnetic interference fields, and/or the control unit suppresses the delivery of stimulation or initiates a sub-threshold or zero intensity delivery of stimulation when an intrinsic event was detected by the detection unit of the control unit and/or was identified by the reconstruction of detection gaps. Sub-threshold intensity and stimulation impulses are those that are below a predeterminable and/or preselectable detection threshold, while the zero-intensity stimulations are performed in the absence of intensity or are only triggered.

It is especially preferred that the control unit has a priority switch that also allows temporary therapy in timeframes, in which electromagnetic interferences have been detected by the unit for recognition of electromagnetic interferences, whereby the priority switch can always be activated and/or can only be activated when an electromagnetic interference has been detected by the unit for recognizing electromagnetic interferences and the interference is below at least one predeterminable sensor measurement value and/or at least one predeterminable indicator value. In this context, "predeterminable" is also to be understood in such a way that one of several predetermined sensor measurement values and/or predetermined indicator values are used, depending on the condition of the patient.

It is also preferred that the reconstruction of the measured data between the timeframes without a detected electromagnetic interference has at least one of the following characteristics, the detection unit additionally has a blanking unit that blends out outliers of detected measured signals, whereby the blanking unit takes the relaxation behavior of the system such as the system electrode and the input switching circuit, and/or the properties of the interference are taken into consideration such as high frequency interferences such as from RF fields, low frequency interferences such as from gradient fields, for the reconstruction, depending on the length of the interference, a reconstruction method is automatically selected, such as a linear or polynomial interpolation, whereby the derivations at the connection points are consistent with the measured values, for short durations of interference and a pattern recognition of typical measurement curves such as QRS complexes and/or T waves and/or p waves and/or combinations such as the QRS-T section and/or T-P-section and/or P-QRS section, a pattern recognition is used for the reconstruction, which recognizes typical measurement curves and forwards the recognized patterns to the control unit, so that the recognized patterns such as QSR complexes and/or T waves and/or p waves and/or combinations such as the QRS-T section and/or T-P section and/or P-QSR section can be used to trigger and/or retrigger the stimulation unit, and the reconstruction by means of a pattern recognition for average or long defects based on the recognized patterns, such as, but not limited to QRS complexes and/or T waves and/or p waves and/or combinations such as the QRS-T section and/or T-P section and/or P-QRS section, determines a complementary pattern.

It is also preferred that the IMD is switched to an operating condition independent of a signal detection when no signal reconstruction is possible using the detected signals, whereby it occurs, inter alia, but not limited to, in short timeframes without electromagnetic interferences in combination with at least intervals of medium length with electromagnetic interferences.

It is further preferred that at least one of the following steps is initiated in a recognition of electromagnetic interferences, the change into a MRI-safe condition, an extended stay in an MRI-safe condition or a condition that is insensitive to electromagnetic interference fields, and the delivery of electromagnetic impulses for signaling that a medical device, specifically an implant is present in the electromagnetic field, specifically for signaling to an MRI device, with the possibility of transmitting—in addition to the interference—also information in this manner and to make it visible on the monitor of the MRI.

It is also preferred that the unit for recognizing electromagnetic interferences for the detection of electromagnetic fields comprises at least one of the following sensors or indicators, GMR sensor, MagFET sensor, Hall sensor, electro-optical converters as indicator, the monitoring of battery voltage during the capacitor loading processes as indicator, the detection of RF fields as indicator, the detection of magnetic gradient fields as indicator, the detection of currents as indicator that have been induced by electromagnetic fields, the detection of specific vibrations or construction components configured as sensors for the detection of vibrations as indicators that have been induced by Lorentz forces.

BRIEF DESCRIPTION OF THE DRAWINGS

Several aspects of the invention are illustrated in FIGS. 1 through 8.

DETAILED DESCRIPTION OF THE INVENTION

Figure 1:
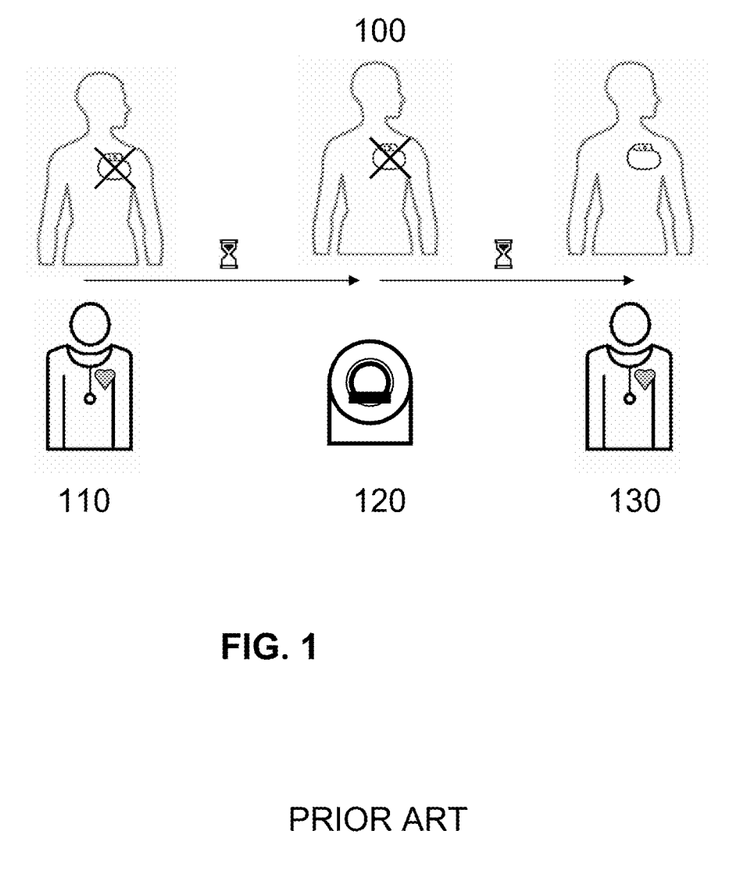
FIG. 1 schematic illustration of the progression of an MRI examination

FIG. 1 describes prior art in which the ICD patient 100 prior to a planned MRT examination receives aftertreatment from a cardiologist and the ICD is switched off 110. With a chronological delay of hours to days, the MRT examination is performed by a radiologist 120. After an additional delay, the patient is again under the care of a cardiologist 130 and the ICD is switched on again. During the entire time from 110 to 130, the patient does not have the protection of the implanted defibrillator and is largely without rhythm monitoring. Currently, this remaining residual risk is accepted, measured by the benefit of the MRT examination.

Figure 2:
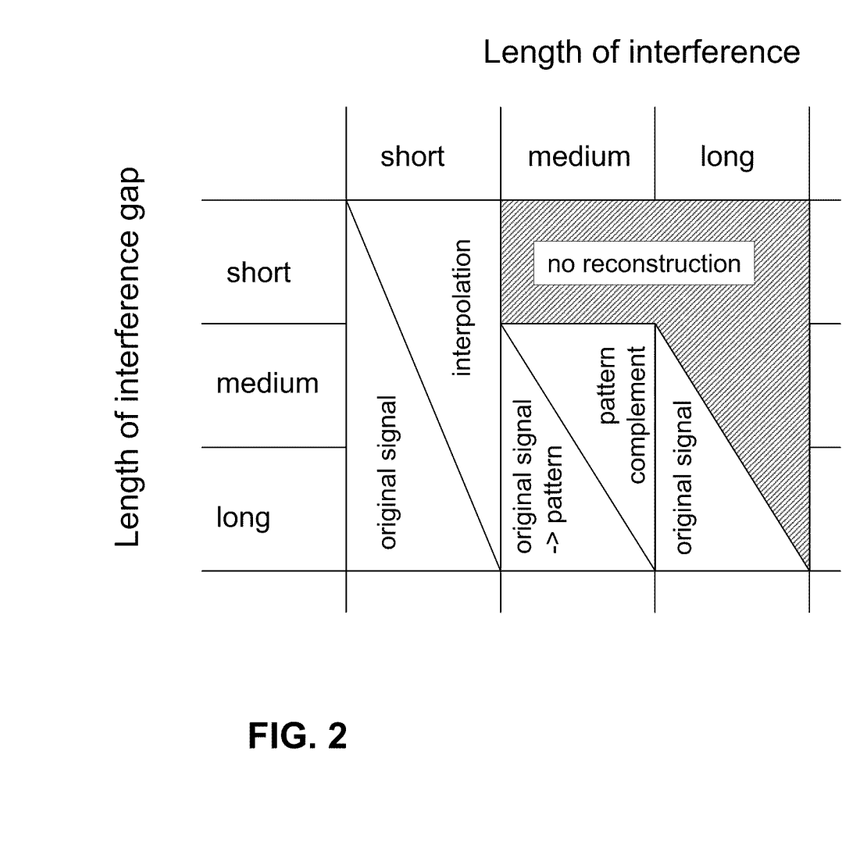
FIG. 2 schematic illustration of the method in relation to the reconstruction and/or interpolation FIG. 3 schematic illustration of a reconstruction and/or interpolation of an IEGM scanning gap FIG. 4 possible implementation FIG. 5 RT predictor FIG. 6 important rules FIG. 7 delay by safety distance FIG. 8 illustration of an at least partially implanted medical device (IMD)

FIG. 2 shows a possible interpretation matrix for possible reactions for different relationships of interference gap length and interference length, whereby the interference gap length describes the intervals without interferences and the interference length the length of the occurring and/or observed electromagnetic interferences. The type of recognition of electromagnetic interferences is of no significance for adjusted IEGM scanning, in principle, all technologies that are suitable for the recognition of electromagnetic interferences are possibilities, particularly, but not limited to GMR sensors, MagFET sensors, Hall sensors, electro-optical converters, the monitoring of battery voltage during capacitor loading processes, the detection of RF fields, the detection of magnetic gradient fields, the detection of currents induced by electromagnetic fields, the detection of specific vibrations or construction components configured for detecting vibrations induced by Lorentz forces. The matrix shows, for example, at which relationships of interference gap length to interference length reconstruction or interpolation occurs, and/or the original signal is used.

Figure 3:
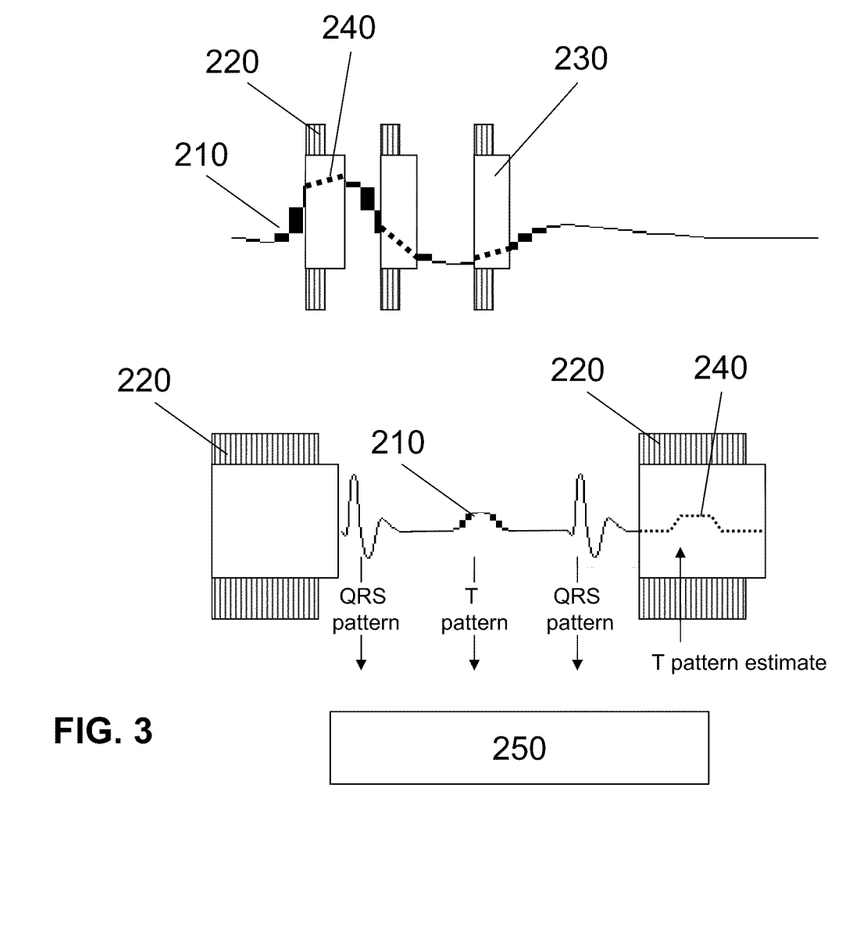

FIG. 3 shows an example of a reconstruction of the original signal 210 during the interferences. The original signal 210 is superimposed by an interference 220 in the upper illustration, as a result of which a blanking window 230 is created, i.e. an interval in which no signals can be detected that extends beyond the interference 220. In blanking window 240, the signal is reconstructed by interpolation, so that a reconstructed section 240 is created.

In the lower illustration in FIG. 3, the measured original signal 210 is forwarded to a cardiac simulator 250, and thus, the gap that is created during blanking interval 230 by interference 220 in the original signal 210 by cardiac simulator 250 is filled in with reconstruction 240. In the selected example, the reconstruction is an estimate of the T pattern. With this method or that which is described above with respect to FIG. 3, the scanning gaps in an IEGM can be filled in.

Figure 4:
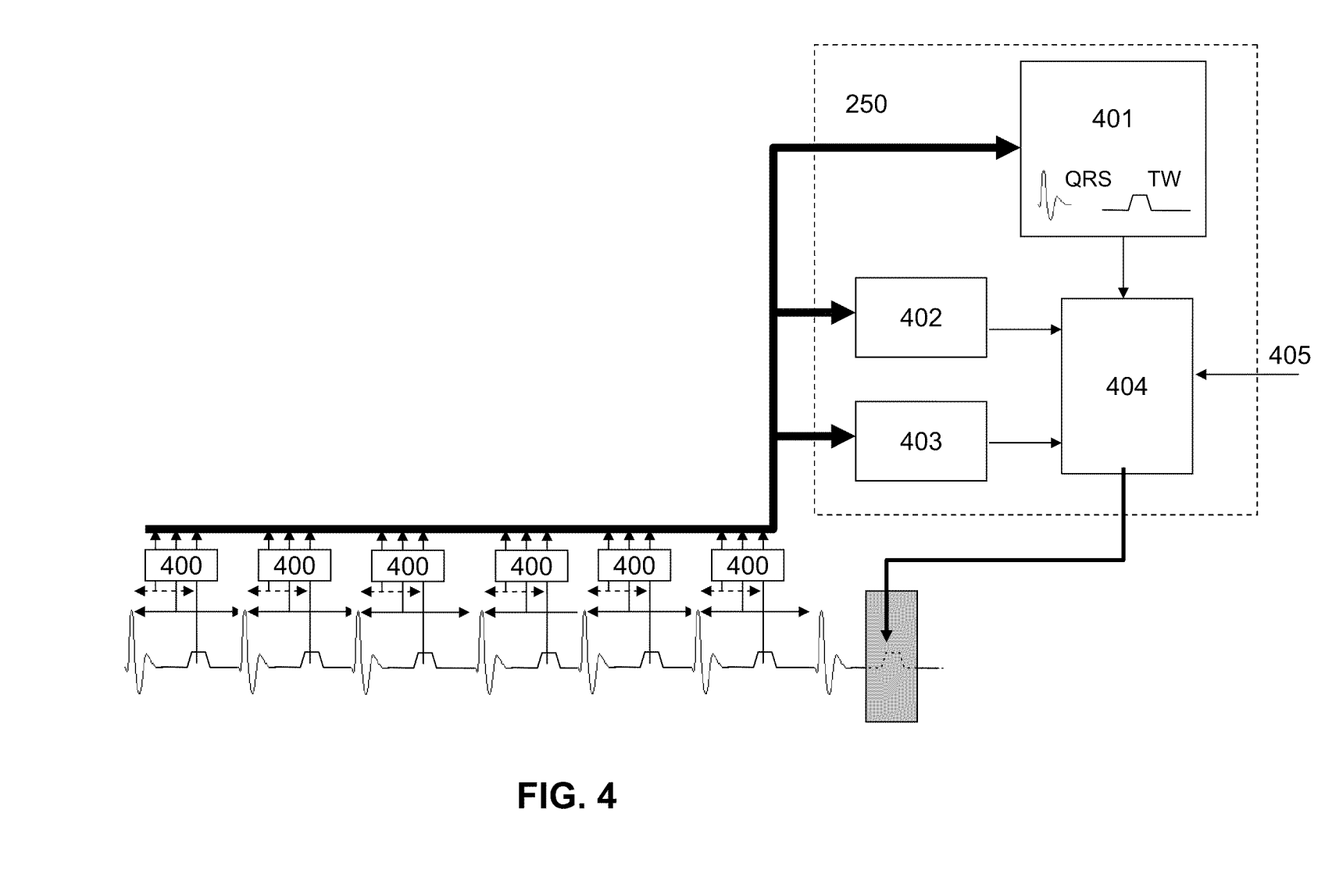

FIG. 4 describes one embodiment. Metric extractors 400 measure continually or by a trigger such as, for example, triggered by the interference field detector of Signal 405 are cardiac cycles with respect to RR intervals, RT intervals, QRS amplitude, -QRS width, QRS area, further T wave amplitude, T wave width, T wave area, as well as morphologies, but not limited to such. These are components of the input information for the cardiac simulator 250, in an implementation according to the invention that is particularly preferred consisting of a morphology database 401, a RR predictor 402 and RT predictor 403. Suitable to the prior history (for example memory depth) the following RR and RT interval is estimated so that such is immediately available in the event of an impending interference. Likewise, based on the input information, the database prepares the morphologies (as standard curves, for example, for QRS waves or T waves or T wave reconstruction), which for a similar preceding morphology sequence has in the past once before followed this pattern (as per the highest probability). With these results of the RR predictor and the RT predictor, this pattern is then scaled and positioned. This is realized by reconstructor 404.

Figure 5:
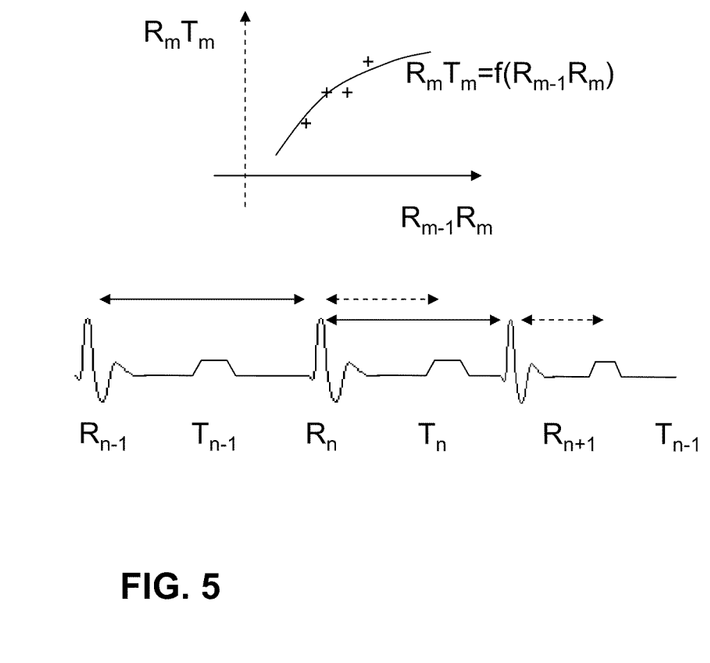

FIG. 5 explains the RT predictor. Each RT interval, corresponding to depth of memory is entered as ordinate above the preceding RR interval as abscissa. According to the applicable law, the currently valid restitution curve is fitted (for example, method of the smallest error squares). With that, the RT interval of the subsequent cardiac cycle can be determined. This process can be realized as sliding segment or blockwise.

The RR predictor (not shown) can, for example, be realized as a time series model with the following calculation formula.

$$R_n R_{n+1} = \sum_{i=1}^{N} a_i R_{n-i} R_{n-i+1}$$

In addition to RR intervals, an expanded realization also considers RT intervals, QRS amplitude, QRS width, QRS area, further T wave amplitude, T wave width, T wave area, as well as morphologies (for example morphology classes and/or indices such as, for example, defined by US 2006/0047216 A1, but not limited to such). Likewise, a further expanded realization also provides nonlinear interconnection of the input information.

In a particularly preferred realization, the reconstructor selects the morphology of the signal section that is to be estimated (for example QRS complex or T wave, etc.) from the database and scales and positions such on the time axis into the missing signal section as per the estimated RT and RR interval values. Amplitude scaling takes place based on the relationships that were obtained from previous signal sections. Thus, for example, the amplitude of the reconstructed T wave is scaled by percentage with respect to the previous R wave, perhaps also taking average values of previous R waves as well as previous T wave amplitudes into consideration.

Figure 6A:
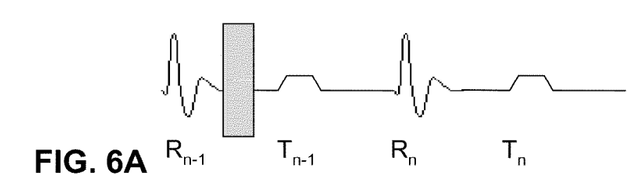
Figure 6B:
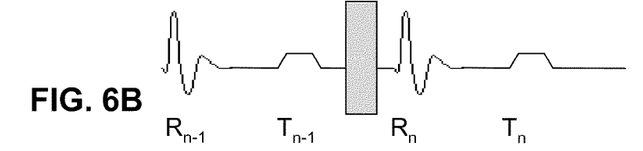

As illustrated in FIG. 6, in the following, the most important rules that are implemented in the particularly preferred implementation of the reconstructor (but not limited to such) are described. The blanking signal 405 defines the sections that are to be reconstructed:

In cases a) and b) only short signal sections are on isoelectric lines of the IEGMs are defective. Here, the missing signal section is connected with a straight line that connects the last point before the interference with the first point after the interference. A further solution is provided by a curve line of the lowest order, the first derivation of which is constant at the contact points.

Figure 6C:
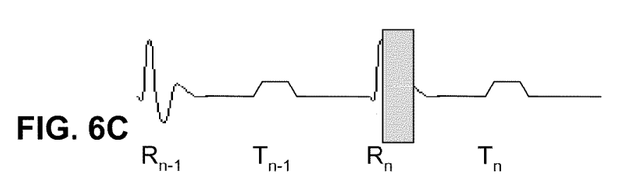
Figure 6D:
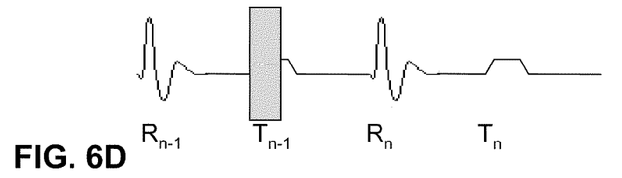

Cases c) and d) show examples where a QRS or T wave section is only partially deficient. These are complemented by the reconstructor with a pattern that would be most likely to occur at this point given similar previous history of the signal.

Figure 6E:
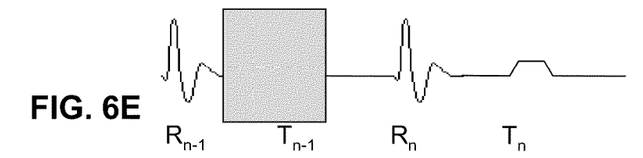

In case e) the RT predictor estimates the RT time, the T wave morphology is selected from the database that would follow with the greatest likelihood at this point, given a similar previous history of the signal.

Figure 6F:
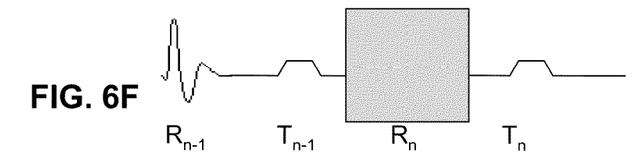

In case f) the RR predictor estimates the RR time, the QRS morphology is selected from the database bank that would follow with the greatest likelihood at this point given a similar previous history of the signal.

Figure 6G:
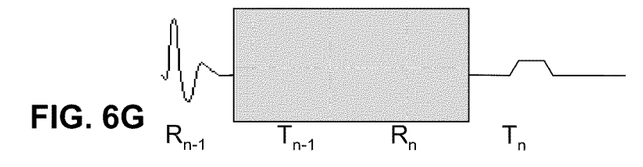

In case g), the following T and QRS are estimated. In the implementation in which the RR predictor also needs the previous RT interval, the value that is estimated by the RT predictor is used for such.

In cases f) and g), in a particularly preferred realization, the missing point in time Rn is calculated not only from the RR predictor, but is additionally determined by the restitution curve, specifically by the solution of the nonlinear equation system:

$$Rn-1Rn+RnTn=b$$

$$RnTn=f(Rn-1Rn)$$

Thereby, b is known, as the signal at the points in time Rn−1 and Tn is not interrupted.

The two results for Rn−1Rn, obtained as a result of the RR predictor on the one hand, and on the other, because of the above mentioned method are interlinked in a further preferred implementation into an average value that then provides the valid point in time Rn.

Figure 6H:
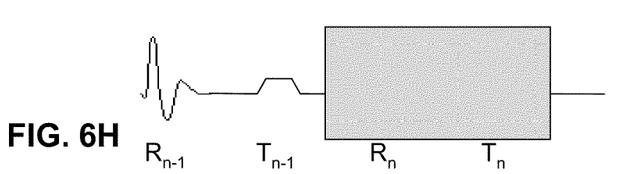

In the case h), first the next QRS is estimated. This RR interval then uses the RT predictor for estimating the next RT time.

Figure 6I:
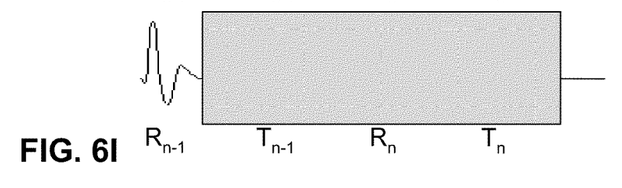

In case i) this continues as it does in cases g and h. The longer the interrupted signal section, the less precise will be the reconstruction, that is why starting at a predeterminable interference length switching takes place into a mode providing therapy for the patient without needing the IEGM signal. In a preferred implementation, this is a fixed frequency stimulation, for example, D00, V00 or A00 mode.

Figure 7:
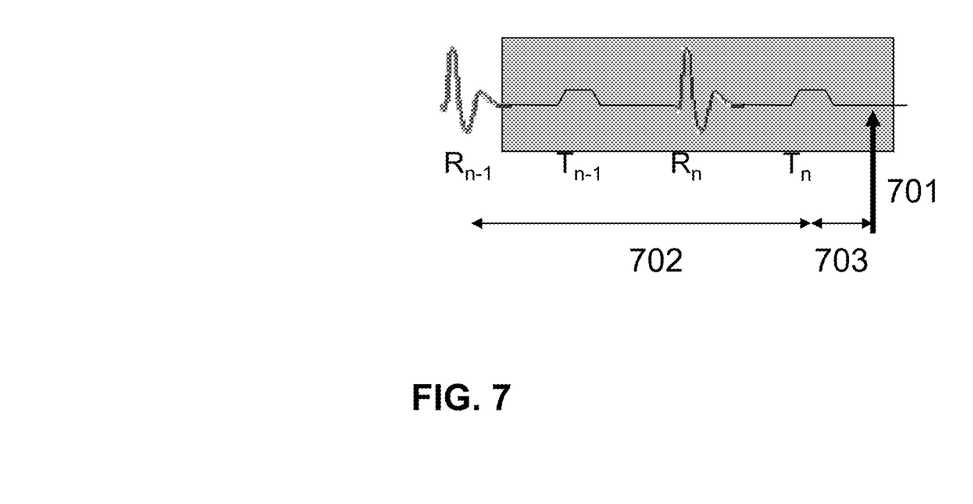

If the interference lasts for a long time, it can no longer be determined if there is any cardiac activity. Therefore, in accordance with the invention, after the watchdog counter 702 has run its course, a safety stimulus 701 is provided. By considering the RR and RT predictor, the position of the vulnerable phase is thereby estimated in which no stimulation may occur, as this otherwise could trigger arrhythmia. Therefore, after the operation of the watchdog counter has run its course, if necessary, the delivery of this stimulus is further delayed by a safety distance 703 (FIG. 7).

Figure 8:
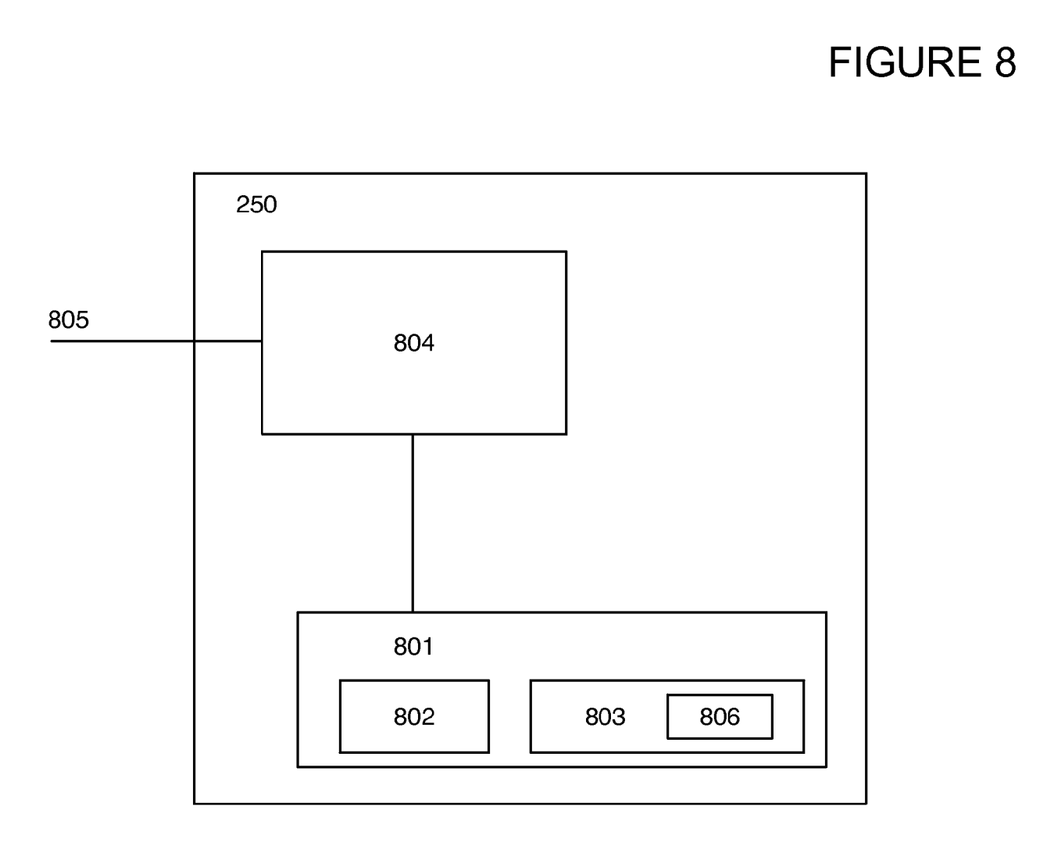

FIG. 8 illustrates at least partially implanted medical device (IMD) 250 that includes at least one unit for recognizing electromagnetic interferences 801, containing at least one sensor or indicator for electromagnetic interference fields 802 and at least one timer 803, at least one control unit 804 that can be connected with the unit for recognizing electromagnetic interferences, at least one electrode line 805 that is connected with the control unit, and that is provided with an electrode at the other end that is in contact with the body tissue, and whereby the electrode either extends into the interior of the body or is located on the surface of an implant, whereby the control unit permits the delivery of electrical stimulation impulses by the at least one electrode only in timeframes, in which no electromagnetic interferences are recognized and/or the control unit performs a reconstruction of the electrical measurements captured by the at least one electrode for the timeframes in which the electromagnetic interferences are recognized. It is also preferred that the timer 803 has a storage device 806 that is configured for storing time differences such as therapy intervals and/or intervals of intrinsic system events.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An at least partially implantable medical device comprising:
    at least one unit configured to recognize electromagnetic interference comprising:
        at least a sensor or indicator for electromagnetic interference fields and
        at least one timer,
    at least one control unit coupled with the at least one unit configured to recognize electromagnetic interference;
    at least one electrode line that is connected with the at least one control unit on a first end and which comprises an electrode at a second end opposite of said first end, that is in contact with body tissue and wherein the electrode either extends into an interior of a body or is located on a surface of the at least partially implantable medical device;
    wherein the at least one control unit is configured to:
        deliver electrical stimulation impulses via the at least one electrode line only in timeframes in which no electromagnetic interferences are recognized and/or perform a reconstruction of the electrical measurements captured by the at least one electrode line for timeframes in which electromagnetic interferences are recognized; and wherein the at least one control unit is configured to perform a calculation to calculate a point in time for a next therapy to be delivered by the at least partially implantable medical device based on data obtained from said at least one timer.

2. The at least partially implantable medical device according to claim 1 wherein
the at least partially implantable medical device comprises:
an external cardiac pacemaker and/or external defibrillator or implanted cardiac pacemaker and/or defibrillator/cardioverter and/or a cardiac resynchronization therapy device,
a cardiac support system such as a cardiac support pump,
an artificial heart,
a neurostimulator,
an implanted monitoring device (patient monitor),
an implanted medication pump,
an implanted fluid pump, and/or
an external heart-lung system; and,
wherein the at least one control unit selects an operating mode of the at least partially implantable medical device based on
detected electromagnetic interference and/or
measured values detected by the at least one electrode and/or
reconstructed measured values from predeterminable operating conditions.

3. The at least partially implantable medical device according to claim 1, wherein the at least one timer comprises a storage device that is configured to save time differences comprising therapy intervals and/or intervals of intrinsic system events.

4. The at least partially implantable medical device according to claim 3, wherein said therapy intervals comprises a preceding therapy interval.

5. The at least partially implantable medical device according to claim 3, wherein the storage device is configured as a First In First Out or FIFO device.

6. The at least partially implantable medical device according to claim 1, wherein said calculation of the point in time for a next therapy is based on:
an estimation of a cardiac rhythm and/or
a heart simulator.

7. The at least partially implantable medical device according to claim 1, wherein said calculation is based on an approximation model of a cardiac restitution and/or a linear or nonlinear time series model and/or on a weighted average of n preceding time differences where n is larger than or equal to 1.

8. The at least partially implantable medical device according to claim 1, wherein
the calculation of the point in time for the next therapy includes avoidance of vulnerable phases of a cardiac stimulation cycle and/or
parameters for calculation models of a point in time for therapy are programmable and/or
models for calculation of the point in time for therapy include measurements from an intracardiac electrogram or IEGM and/or electrocardiogram or EKG and/or reconstructed IEGM measurements in the calculation, wherein EKG data are determined by external tools and are made available to the at least partially implanted medical device and wherein data from a patient history are included from available information sources which comprise patient files, patient databases and/or patient device, and/or
the calculation is based on parameters and measurements stored in the at least partially implantable medical device, and/or
the calculation is based on parameters and measurements stored in the at least partially implantable medical device when no electromagnetic interference is detected.

9. The at least partially implantable medical device according to claim 1, further comprising a stimulation unit configured to be triggered and/or retriggered, specifically by measurements in timeframes without detected electromagnetic interference fields and/or by reconstructed measured data between timeframes without the detected electromagnetic interference fields, and/or the at least one control unit suppresses delivery of stimulation or initiates a sub-threshold or zero-intensity delivery of stimulation, when an intrinsic event is detected by the at least one control unit and/or was identified by reconstruction of detection gaps.

10. The at least partially implantable medical device according to claim 9, wherein the control unit has a priority switch configured to temporarily permit therapy in timeframes in which electromagnetic interferences are detected by the at least one unit which is configured to recognize electromagnetic interference, wherein the priority switch is configured to be activated when an electromagnetic interference is detected by at least one unit and when electromagnetic interference is below at least one predeterminable measured sensor value and/or at least one predeterminable indicator value.

11. The at least partially implantable medical device according to claim 1, wherein said at least one control unit is configured for reconstruction of measured data between timeframes without detected electromagnetic interference, wherein said at least one control unit is further configured to:
blend out outliers of detected measured signals,
perform reconstruction, depending on a length of an interference,
utilize pattern recognition in said reconstruction, or
determine a complementary pattern for the reconstruction via said pattern recognition for medium or long defects based on a recognized pattern.

12. The at least partially implantable medical device according to claim 1, wherein the at least partially implantable medical device is configured to switch into an operating condition independent of said recognized electromagnetic interferences, when reconstruction of the electrical measurements from said electromagnetic interferences is not possible.

13. The at least partially implantable medical device according to claim 1, wherein upon recognition of electromagnetic interference, the at least one control unit is configured to:
switch into a magnetic resonance imaging safe condition,
remain for a prolonged time in said magnetic resonance imaging safe condition or a state that is insensitive to electromagnetic interference fields, and
emit electromagnetic pulses to another device to signal that said at least partially implantable medical device is present in an electromagnetic field.

14. The at least partially implantable medical device according to claim 1, wherein the unit configured to recognize electromagnetic interference for the detection of electromagnetic fields comprises at least one of the following sensors or indicators:
GMR sensor, MagFET sensor,
Hall sensor,
electro-optical converter,
battery voltage sensor configured to monitor voltage during capacitor charging,
RF field detector,
magnetic gradient field detector,
current detector for currents induced by electromagnetic fields,
vibration detector, for detection of vibrations induced by Lorentz forces.

15. An at least partially implantable medical device comprising:
  at least one unit configured to recognize electromagnetic interference comprising:
    at least a sensor or indicator for electromagnetic interference fields and
    at least one timer,
  at least one control unit coupled with the at least one unit configured to recognize electromagnetic interference;
  at least one electrode line that is connected with the at least one control unit on a first end and which comprises an electrode at a second end opposite of said first end, that is in contact with body tissue and wherein the electrode either extends into an interior of a body or is located on a surface of the at least partially implantable medical device;
  wherein the at least one control unit is configured to:
    deliver electrical stimulation impulses via the at least one electrode line only in timeframes in which no electromagnetic interferences are recognized and/or
    perform a reconstruction of the electrical measurements captured by the at least one electrode line for timeframes in which electromagnetic interferences are recognized;
  wherein said at least one control unit is configured for reconstruction of measured data between timeframes without detected electromagnetic interference, wherein said at least one control unit is further configured to:
    blend out outliers of detected measured signals,
    perform reconstruction, depending on a length of an interference,
    utilize pattern recognition in said reconstruction, or
    determine a complementary pattern for the reconstruction via said pattern recognition for medium or long defects based on a recognized pattern.

* * * * *